US00PP18374P2

(12) United States Plant Patent
Hofmann

(10) Patent No.: US PP18,374 P2
(45) Date of Patent: Jan. 1, 2008

(54) ***GERANIUM* PLANT NAMED 'PACFOX'**

(50) Latin Name: *Pelargonium×hortorum*
Varietal Denomination: Pacfox

(75) Inventor: Christa Hofmann, Radeburg (DE)

(73) Assignee: Elsner PAC Jungpflanzen, Dresden (DE)

( * ) Notice: Subject to any disclaimer, the term of this patent is extended or adjusted under 35 U.S.C. 154(b) by 0 days.

(21) Appl. No.: 11/358,929

(22) Filed: Feb. 17, 2006

(51) Int. Cl.
*A01H 5/00* (2006.01)

(52) U.S. Cl. ..... Plt./329
(58) Field of Classification Search ..... Plt./329, Plt./325
See application file for complete search history.

(56) References Cited

PUBLICATIONS

UPOV–ROM GTITM, Plant Variety Database, 2006/04, GTI Jouve Retrieval Software, Citation for *Pelargonium* 'Pacfox' one page.*

Elsner Pac Jungpflanzen GbR Contact retrieved from the Internet on Mar. 13, 2007. Retrieved at <http://www.pac–elsner.com/uk/kontakt/kontakt–index.html> 2 pages.*

* cited by examiner

*Primary Examiner*—Kent Bell
*Assistant Examiner*—June Hwu
(74) *Attorney, Agent, or Firm*—C. A. Whealy

(57) ABSTRACT

A new and distinct cultivar of Zonal *Geranium* plant named 'Pacfox', characterized by its upright, rounded and uniform plant habit; freely basal branching and flowering habit; leaves with a distinct zonation pattern; red purple-colored flowers; and good garden performance.

2 Drawing Sheets

Botanical designation: *Pelargonium×hortorum.*
Cultivar denomination: 'Pacfox'.

BACKGROUND OF THE INVENTION

The present invention relates to a new and distinct cultivar of Zonal *Geranium* plant, botanically known as *Pelargonium×hortorum,* and hereinafter referred to by the name 'Pacfox'.

The new Zonal *Geranium* is a product of a planned breeding program conducted by the Inventor in Dresden, Germany. The objective of the breeding program was to develop new uniform Zonal *Geraniums* with attractive flower coloration and high cutting yield.

The new Zonal *Geranium* originated from a cross-pollination made by the Inventor in 2001 of two unnamed proprietary selections of *Pelargonium×hortorum,* not patented. The cultivar Pacfox was discovered and selected by the Inventor as a flowering plant within the progeny from the stated cross-pollination in a controlled environment in Dresden, Germany in 2002.

Asexual reproduction of the new cultivar by terminal cuttings in a controlled environment in Dresden, Germany since 2002 has shown that the unique features of this new Zonal *Geranium* are stable and reproduced true to type in successive generations of asexual reproduction.

SUMMARY OF THE INVENTION

The following traits have been repeatedly observed and are determined to be the unique characteristics of 'Pacfox'. These characteristics in combination distinguish 'Pacfox' as a new cultivar and distinguish it from other known Zonal *Geranium* cultivars:

1. Upright, rounded and uniform plant habit.
2. Freely basal branching and flowering habit.

3. Leaves with a distinct zonation pattern.
4. Red purple-colored flowers.
5. Good garden performance.

Plants of the new Zonal *Geranium* differ primarily from plants of the parent selections in flower color and flower form.

Plants of the new Zonal *Geranium* can be compared to plants of the cultivar Pacshovi, disclosed in U.S. Plant Pat. No. 14,210. In side-by-side comparisons conducted in Dresden, Germany, plants of the new Zonal *Geranium* differed from plants of the cultivar Pacshovi in the following characteristics:

1. Plants of the new Zonal *Geranium* were more vigorous and larger than plants of the cultivar Pacshovi.
2. Plants of the new Zonal *Geranium* had larger leaves than plants of the cultivar Pacshovi.
3. Plants of the new Zonal *Geranium* had smaller flowers than plants of the cultivar Pacshovi.
4. Plants of the new Zonal *Geranium* and the cultivar Pacshovi differed in flower color.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Flower and foliage colors in the photographs may differ slightly from the color values cited in the detailed botanical description which accurately describe the colors of the new Zonal *Geranium.*

The photograph on the first sheet comprises a side perspective view of a typical flowering plant of 'Pacfox' grown in a container.

The photograph on the second sheet is a close-up view of a typical flower of 'Pacfox'.

DETAILED BOTANICAL DESCRIPTION

Plants of the cultivar Pacfox have not been observed under all possible environmental conditions. The phenotype may vary somewhat with variations in environment, such as temperature and light intensity, without, however, any variance in genotype.

The aforementioned photographs, following observations and averaged measurements describe plants grown during the spring in containers in Dresden, Germany, and under commercial practice in a glass-covered greenhouse with day temperatures about 18° C., night temperatures about 16° C. and light levels ranging from 15 to 100 kilolux. Plants used for the photograph and the description were about three months old. In the following description, color references are made to The Royal Horticultural Society Colour Chart, 1995 Edition, except where general terms of ordinary dictionary significance are used.

Botanical classification: *Pelargonium×hortorum* cultivar Pacfox.

Parentage:

*Female, or seed, parent.*—Unnamed proprietary selection of *Pelargonium×hortorum,* not patented.

*Male, or pollen, parent.*—Unnamed proprietary selection of *Pelargonium×hortorum,* not patented.

Propagation:

*Type cutting.*—Terminal cuttings.

*Time to initiate roots, summer.*—About 18 days at 22° C.

*Time to initiate roots, winter.*—About 22 days at 22° C.

*Time to produce a rooted young plant, summer.*—About 25 days at 22° C.

*Time to produce a rooted young plant, winter.*—About 30 days at 22° C.

*Root description.*—Fine, fibrous; white in color.

*Rooting habit.*—Freely branching, dense.

Plant description:

*General appearance.*—Upright, rounded and uniform plant habit; uniform; densely foliated.

*Growth and branching habit.*—Moderately vigorous growth habit. Freely basal branching habit with about ten lateral branches per plant; pinching is not required.

*Plant height, to top of umbels.*—About 30 cm.

*Plants height, to top of foliar plane.*—About 20 cm.

*Plant width.*—About 40 cm.

*Lateral branches.*—Length: About 10 cm. Diameter: About 8 mm. Internode length: About 1.5 cm. Texture: Pubescent. Color: 144A.

*Foliage description.*—Arrangement: Alternate or opposite; simple. Length: About 5 cm. Width: About 8 cm. Shape: Reniform. Apex: Rounded. Base: Cordate; closed. Margin: Bicrenate. Venation pattern: Palmate. Texture, upper and lower surfaces: Pubescent. Color: Developing and fully expanded foliage, upper surface: 146A; venation, 144A. Developing and fully expanded foliage, lower surface: 146B; venation, 146C. Zonation pattern: Intensity: Distinct. Location of zone from margin: About 7 mm. Width: About 1.5 cm. Color: 147A. Petiole: Length: About 5 cm. Diameter: About 2 mm. Texture, upper and lower surfaces: Pubescent. Color, upper and lower surfaces: 144A.

Flower description:

*Flower arrangement.*—Red purple-colored flowers; semi-double rotate flowers arranged in rounded hemispherical umbels arising from apical leaf axils. Umbels displayed upright above the foliage on strong peduncles. Flowers face upright to outwardly; flowers slightly cupped and uniform. Flowers persistent. Flowers not fragrant.

*Quantity of flowers.*—Freely flowering habit; about 15 umbels per plant, about 20 flower buds and open flowers per umbel.

*Flowering season.*—Year-round under greenhouse conditions. In the garden in Dresden, Germany, flowering is continuous from April until frost in the fall.

*Flower longevity.*—Individual flowers last about six to ten days and umbels last about three to four weeks on the plant.

*Umbel height.*—About 7 cm.

*Umbel diameter.*—About 15 cm.

*Flower diameter.*—About 5 cm.

*Flower depth (height).*—About 2.5 cm.

*Flower buds.*—Length: About 7 mm. Diameter: About 6 mm. Shape: Elliptic. Color: 146C.

*Petals and petaloids.*—Quantity per flower: About six to nine. Length: About 2 cm to 3 cm. Width: About 0.5 cm to 3 cm. Shape: Obovate; petaloids, irregular. Apex: Rounded. Base: Attenuate. Margin: Entire. Texture, upper and lower surfaces: Smooth, glabrous; velvety. Color: When opening and fully opened, upper surface: 66A; towards the margin, 45B; blotch, 41A; towards the base, close to 155D; venation, 45B; color becoming closer to 66A with development. When opening and fully opened, lower surface: 66C; towards the base, close to 155D; venation, 45B.

*Sepals.*—Quantity per flower: Five, arranged in a single whorl. Length: About 9 mm. Width: About 3 mm. Shape: Lanceolate. Apex: Acute. Base: Attenuate. Margin: Entire. Texture, upper and lower surfaces: Pubescent. Color, upper and lower surfaces: 144A.

*Peduncle (umbel stem).*—Length: About 10 cm. Diameter: About 5 mm. Strength: Strong. Aspect: Upright. Texture: Pubescent. Color: 146A.

*Pedicel (individual flower stem).*—Length: About 3 cm. Diameter: About 2 mm. Strength: Moderately strong; flexible. Texture: Pubescent. Color: 146C.

*Reproductive organs.*—Androecium: Stamen quantity per flower: About nine. Filament: Less than 1 mm; white in color. Anther length: About 2 mm. Anther shape: Oblong. Anther color: 172B. Pollen amount: Abundant. Pollen color: 172B. Gynoecium: Pistil quantity per flower: One. Pistil length: About 7 mm. Stigma shape: Five-parted. Stigma color: 60B. Style length: About 2 mm. Style color: 60D. Ovary color: 148C. Seeds: Length: About 3 mm. Diameter: About 1 mm. Color: 165A.

Disease/pest resistance: Plants of the new Zonal *Geranium* have not been observed to be resistant to pathogens and pests common to Zonal *Geraniums*.

Garden performance: Plants of the new Zonal *Geranium* have been observed to tolerate rain, wind, and temperatures ranging from about 0° C. to about 35° C. and have demonstrated good garden performance.

It is claimed:

1. A new and distinct cultivar of Zonal *Geranium* plant named 'Pacfox', as herein illustrated and described.

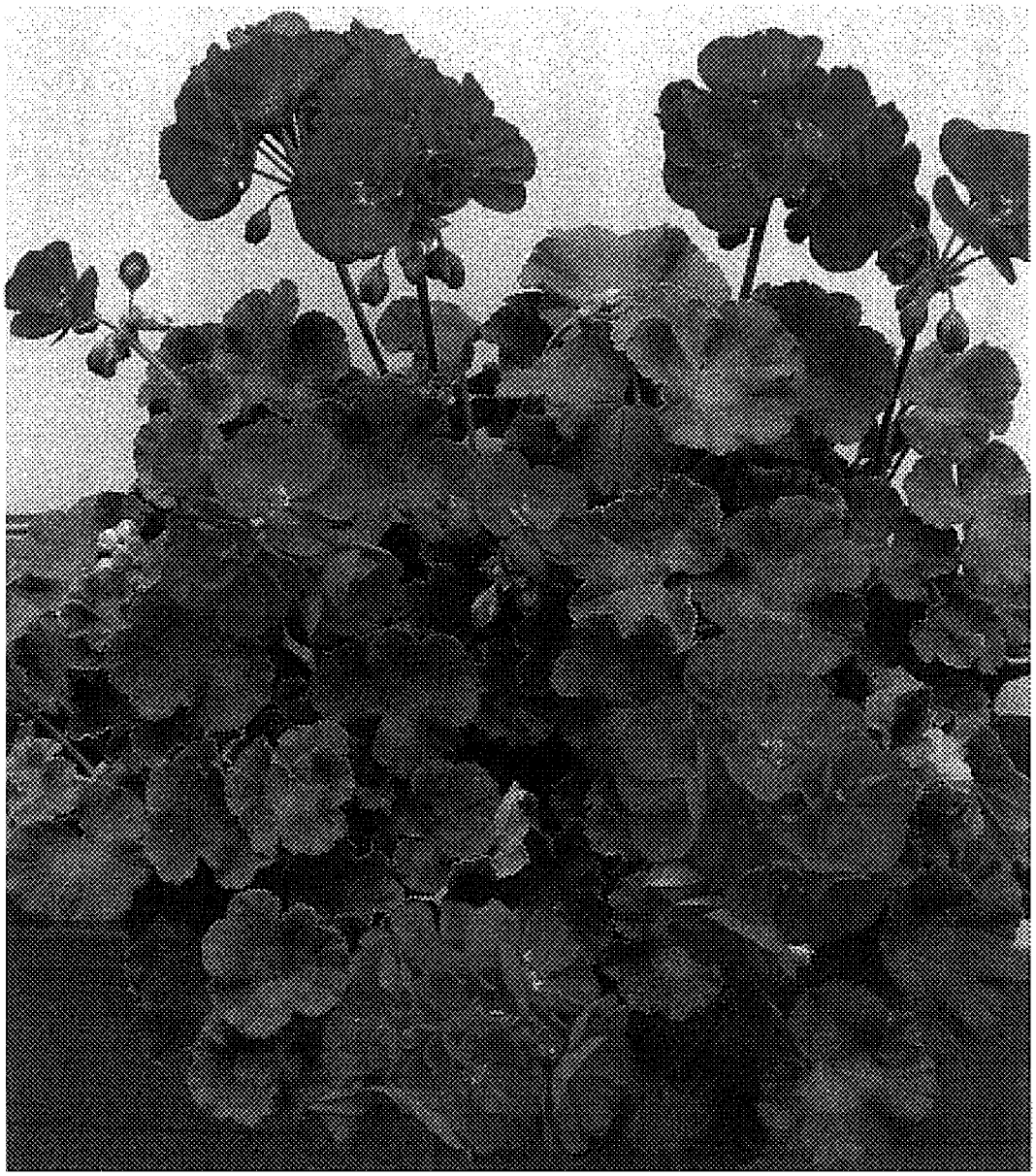

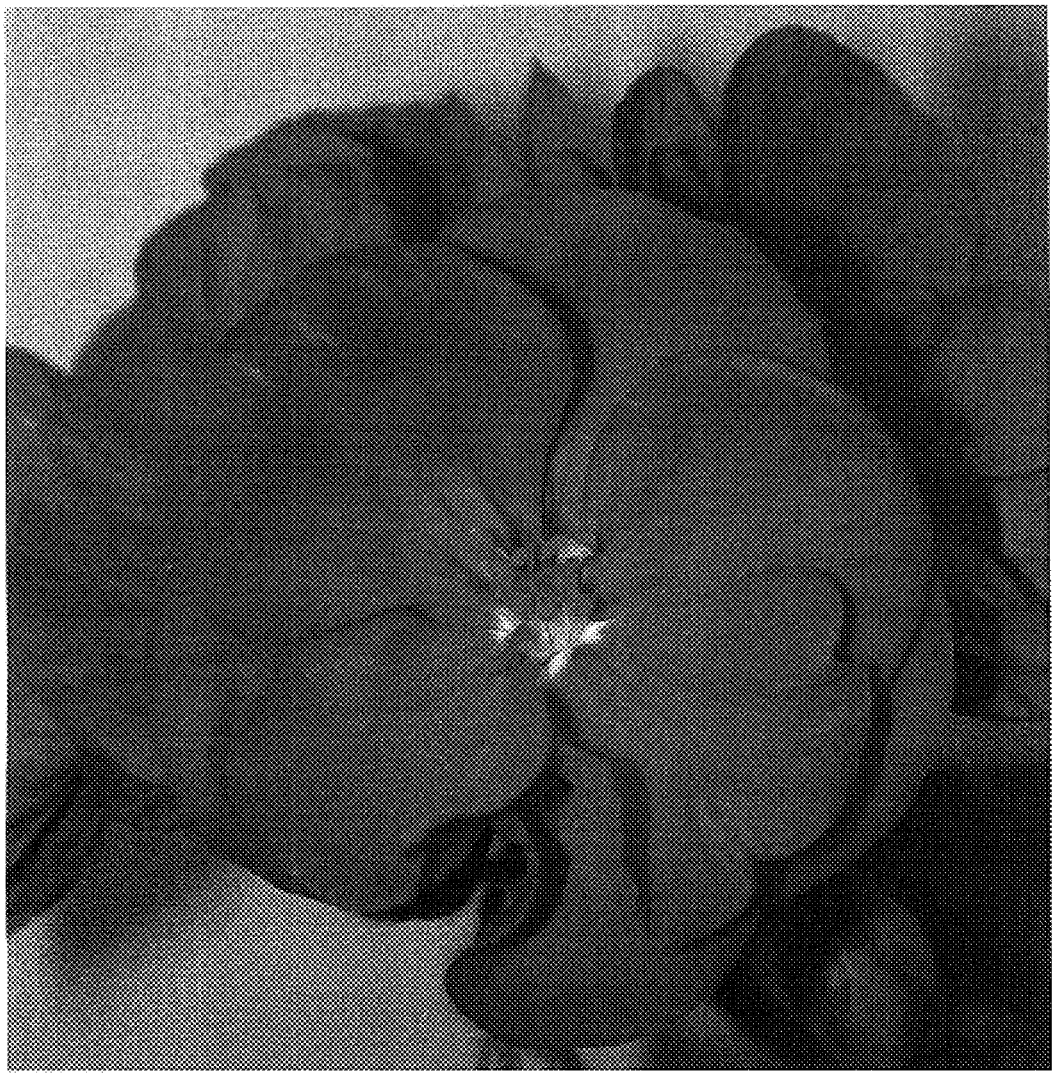

* * * * *